Figure 1:
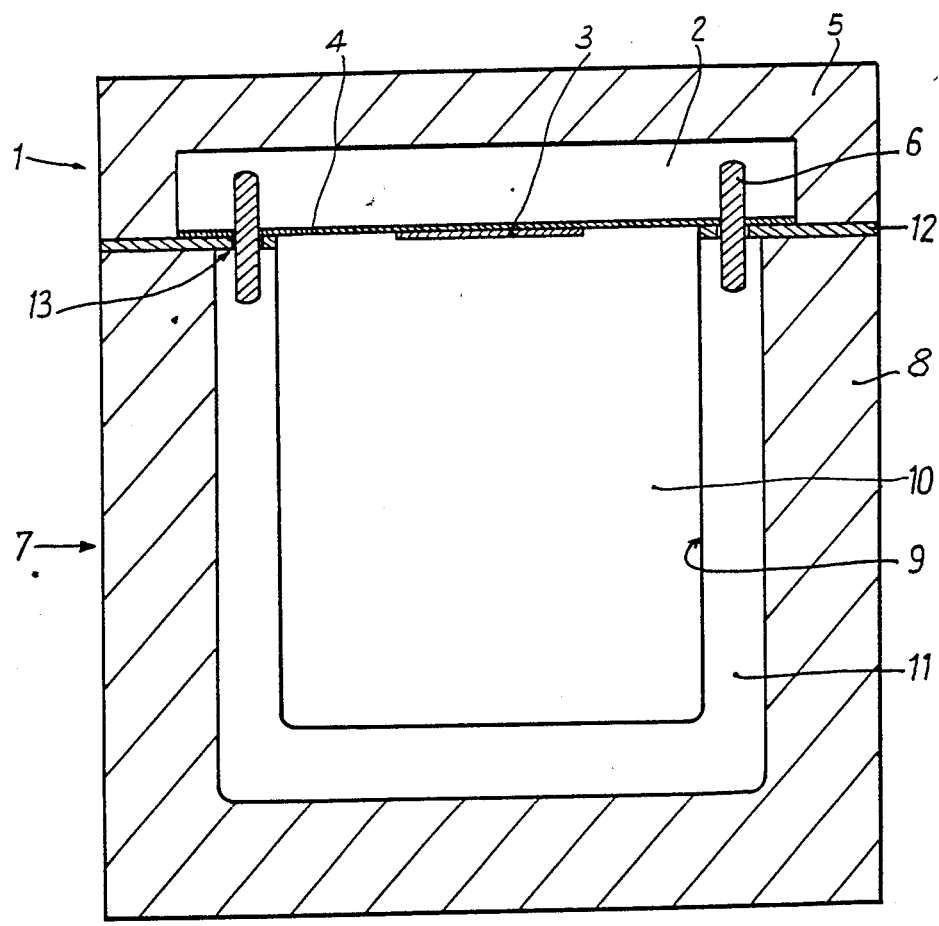

United States Patent [19]

Guilhem et al.

[11] Patent Number: 4,958,506

[45] Date of Patent: Sep. 25, 1990

[54] CONTAINER FOR TRANSPORTING GRAFTS

[76] Inventors: Jacques R. J. Guilhem, 28 rue du Commandant Henry Vesco, 78 310 Sainte-Adresse; Roger L. L. Wengler, 37 rue Mac Orlan, 76 600 Le Havre, both of France

[21] Appl. No.: 319,294

[22] Filed: Mar. 6, 1989

[30] Foreign Application Priority Data

Mar. 7, 1988 [FR] France .................................. 88 02845

[51] Int. Cl.⁵ .................................................. F25D 3/08
[52] U.S. Cl. ................................... 62/457.2; 62/119; 62/371; 62/432; 62/529
[58] Field of Search ..................... 62/457.2, 260, 457.1, 62/431, 432, 437, 430, 356, 371, 372, 529, 119

[56] References Cited

U.S. PATENT DOCUMENTS

| | | | |
|---|---|---|---|
| 1,571,438 | 2/1926 | Schopf | 62/457.2 X |
| 1,641,192 | 9/1927 | Olin | 62/457.2 X |
| 3,195,619 | 7/1965 | Tippmann | 62/119 X |
| 3,390,541 | 7/1968 | Johnson et al. | 62/119 X |
| 3,406,532 | 10/1968 | Rownd et al. | 62/457.2 |
| 3,564,727 | 2/1971 | Fraser | 62/333 |
| 4,135,371 | 1/1979 | Kesselring et al. | 62/119 X |
| 4,240,268 | 12/1980 | Yuan | 62/260 |
| 4,322,954 | 4/1982 | Sheehan | 62/457.1 |
| 4,346,569 | 8/1982 | Yuan | 62/260 |
| 4,498,312 | 2/1985 | Schlosser | 62/457.2 |
| 4,530,816 | 7/1985 | Douglas-Hamilton | 62/457.2 X |

FOREIGN PATENT DOCUMENTS

| | | | |
|---|---|---|---|
| 3627201 | 9/1987 | Fed. Rep. of Germany . | |
| 2581513 | 8/1986 | France . | |
| 215203 | 9/1941 | Switzerland | 62/457.2 |
| 375658 | 8/1961 | Switzerland . | |
| 808690 | 2/1959 | United Kingdom | 62/457.3 |

Primary Examiner—Lloyd L. King
Attorney, Agent, or Firm—Larson and Taylor

[57] ABSTRACT

The invention concerns an isothermic container for transporting grafts at a constant temperature equal to +4° C. For this purpose, the container according to the invention presents a thermal exchanger (6) realizing a thermal flow between a thermal source constituted in particular by ice and water at about 0° C. and disposed preferably in the lid (1) of the container and a volume such as a peripheral enclosure (11).

15 Claims, 3 Drawing Sheets

CONTAINER FOR TRANSPORTING GRAFTS

The present invention relates to an isothermic container intended in particular for transporting grafts, in particular a heart or a heart-lungs assembly, at a constant temperature equal to +4° C.

Recent development of the grafting of organs has revealed the need for a device permitting the transporting of an organ to be transplanted from the hospital of the donor to that of the receiver under the required conditions.

The conditions to be imperatively respected are a constant temperature equal to +4° C. and a total asepsis, it being understood that the graft must be preserved in physiological serum.

The question of the asepsis has been solved in particular by the use of a triple package employing bags of plastics material, one, being absolutely sterile, in contact with the graft, the second constituting a supplementary security, the third outer bag allowing the handling of the graft.

On the other hand, the problem of the imposition and maintenance of the temperature at +4° C. has not heretofore found a satisfactory solution. The transport is effected at the present time in containers of the camping ice-box type in which ice is introduced in sufficient quantity in accordance with the exterior temperature and the duration of the transport. It is therefore clear that it does not concern a true regulation of temperature with all the problems this can produce.

It must be well understood that the solving of this problem cannot be conceived with a large increase in the weight and overall size and a supply of exterior energy, since the ease of transport is an important condition.

The present invention aims at solving this problem by proposing a container which permits, with no increase in size with respect to the containers of the prior art, the obtainment of +4° C. and then an autoregulation at +4° C. for a predetermined sufficient period and which is of a reasonable weight and of low manufacturing cost.

Another object of the invention is to provide a container for transporting grafts at +4° C. which is simple, sturdy and whose operation cannot get out of order.

A further object of the invention is to provide a container for transporting grafts at +4° C. whose autonomy is at least 10 hours under normal exterior temperature conditions.

The invention provides a container formed by a vessel and a lid thermally insulated from the exterior medium, adapted for transporting grafts at +4° C., characterized by a thermal exchanger located in the upper part of the container, preferably in the lower part of the lid, and a peripheral volume filled with water, such as a water jacket or peripheral enclosure, said exchanger ensuring a thermal transfer between a superjacent thermal source at a constant temperature and the layer of water located in the upper part of said volume.

The thermal source is, for example, a source of cold constituted in particular of water and ice at about 0° C. In the case of an exterior temperature higher than +4° C., thermal exchanges occur between the interior of the container and the exterior medium. The water which heats to above +4° C. rises to the upper part of the vessel owing to its lower density relative to that of water at +4° C. A thermal flow in a direction toward the source of cold is therefore established and results in a cooling, essentially by conduction, of this upper layer of water which, in reaching +4° C., will leave place, as the case may be, for the hotter water. In other words, a certain stratification of the water in the vessel will be obtained, the major part of the vessel being at +4° C. and the upper layer of water having a temperature which tends to approach +4° C. The graft therefore always remains in contact with or in the vicinity of water at +4° C.

If the water of the vessel cools to below +4° C., this water rises or remains in the upper part of the vessel owing to a lower density relative to that of the water at +4° C. As the temperature gradient is very low, the thermal flow diminishes and the thermal exchange is stopped and owing to the quasi-absence of convection and the low value of the conduction, a temporary maintenance of the situation is attained.

When the exterior temperature is permanently lower than +4° C., it may be of utility to replace the source of cold with a source of heat.

In any case, the variations in temperature are localized in the region of the thermal exchanger and are therefore without effect on the graft, provided of course that the thermal source is not exhausted. Preferably, the container according to the invention is characterized by the fact that its lid comprises an enclosure for disposing the thermal source and an opening, which closes hermetically, for the introduction of the thermal source.

Preferably, the thermal exchanger is constituted by members constructed from a metal which is a good conductor of hear fixed to the lid and arranged in such a manner as to penetrate the enclosure containing the thermal source and extend beyond the lid in the opposite direction so as to penetrate the upper part of the water jacket or peripheral enclosure. The number and the characteristics of these metal members will depend of course on the dimensions of the container and the thermal exchanges with the exterior medium. However, the invention has the advantage of not being too sensitive to the precision in the choice of the dimensions of these metal members. Care may be taken to provide for these dimensions as a function of the extreme conditions of temperature liable to be encountered, in particular the highest temperatures.

In a particular embodiment of the invention, the members for the thermal exchange are hollow metal studs intended to receive a certain volume of gas in the liquid state, said gas, in the gaseous state, being condensable at around 0° C. The studs are provided with a filler and a valve in the manner for example/of cigarette lighters.

Owing to this realization, the thermal exchanges are accelerated. The heating of the liquid gas in the lower part of the studs causes a conversion of the liquid into gas, the gas passes into the upper free volume of the studs and condenses on the walls of the latter, which are at about 0° C.

The gas employed may be advantageously butane.

Preferably, the metal members forming the thermal exchanger are made from an aluminium/magnesium alloy (AG3 or AG5) insensitive to chlorides in order to permit periodically disinfecting with Javel water.

In one embodiment, the vessel of the container is divided by a partition into a principal enclosure receiving the graft and possibly water between 0° C. and +4° C. and a peripheral enclosure which is open in its upper part so that the metal members realizing the thermal exchanger can penetrate therein when the lid is placed in position.

The partition separating the two enclosures is preferably constituted by a plastics material.

In another advantageous embodiment, the enclosure for disposing the thermal source and the peripheral enclosure are removable relative to insulating walls respectively forming the lid and the vessel.

In both cases, the variations in temperature due to thermal exchanges with the exterior medium will be confined to the region of the peripheral enclosure. The principal enclosure will be practically unaffected by thermal variations.

In order to minimize convection as far as possible while respecting a sufficient insulation of the principal enclosure, the thickness of the peripheral enclosure is chosen to be relatively small, preferably about 40 mm.

In these embodiments, when a graft is placed in the principal enclosure, the peripheral enclosure is for example filled with water at between +1° C. and +4° C. As a variant, it is possible to fill the peripheral enclosure with water at a temperature which takes into account the internal temperature of the graft in question. Knowing the exact volume of the peripheral enclosure and the specific heat of the graft, the temperature of the water intended for the peripheral enclosure is brought to such value that the thermal flow required to bring the graft to +4° C. is largely compensated for without the thermal exchanger needing to intervene very much. An economy of time and source of cold results.

The thermal source, preferably a mixture of water and ice, which is advantageously disposed in the lid and has a relationship with the upper end of the exchanger, may have any geometrical shape. It may or may not be thermally insulated from the vessel. However, preferably, the source extends substantially, above the vessel, on substantially the whole of the width of the vessel, the cavity for the source having a flat bottom so that the most dense part of the water of the water/ice mixture of the source will rest on this bottom whose temperature will tend toward +4° C., thereby completing the peripheral enclosure of water at 4° C.

It will be preferred that the thermal conductors of the exchanger, for example metal rods, upwardly extend a certain distance above the bottom of the source so as to be in contact with the coldest part of the source.

The container according to the invention is preferably cylindrical.

For transporting a heart to be grafted, the container preferably has an outside diameter on the order of 390 mm for an overall height on the order of 470 mm.

For transporting a heart-lungs assembly, the container preferably has an outside diameter on the order of 480 mm for an overall height on the order of 540 mm. The thickness of the peripheral enclosure is on the order of 40 mm as concerns the lateral peripheral part and on the order of 50 mm as concerns the bottom. The heat insulation has a thickness on the order of 50 to 75 mm. The metal rods forming the thermal exchanger are 6 in number and have a diameter of 20 mm for a length of 80 mm.

The invention will now be described in more detail with the aid of the accompanying drawing which presents in FIG. 1, a diametrical section of a cylindrical container according to one embodiment of the invention, the closing device, preferably elastic, of the container not being shown, in FIG. 2, a partial section of another preferred embodiment and, in FIG. 3, a cross section of a portion of a container having a hollow stud containing a liquified gas according to another embodiment.

With reference to FIG. 1, the lid 1 of the container comprises an enclosure 2 for disposing the thermal source and an opening, which is hermetically closed by means of a plug 3 and located in the lower wall 4 of the lid 1. This lid 1 also has a heat insulation 5.

According to FIG. 1, the thermal exchanger is constituted by fixed metal rods 6 fixed to the lower wall 4 of the lid 1 and penetrating the enclosure 2. These rods 6 are diametrically opposed in pairs.

The vessel 7 has a heat insulation 8 which constitutes the frame thereof. It is divided by a partition 9 into a principal enclosure 10 receiving the graft and a peripheral enclosure 11, an insulating annular plate 12 being arranged in the upper part of the peripheral enclosure 11 and fixed to the heat insulation 8. This annular plate 12 has apertures 13 for the passage of the metal rods 6 constituting the thermal exchanger, which rods penetrate the peripheral enclosure 11 when the lid 1 is placed in position. This annular plate 12 permits the hermetic closure of the vessel, while 0-section sealing elements, not-shown, ensure a sealing which is as perfect as possible of the peripheral enclosure in the region of the apertures 13.

Figure 2:
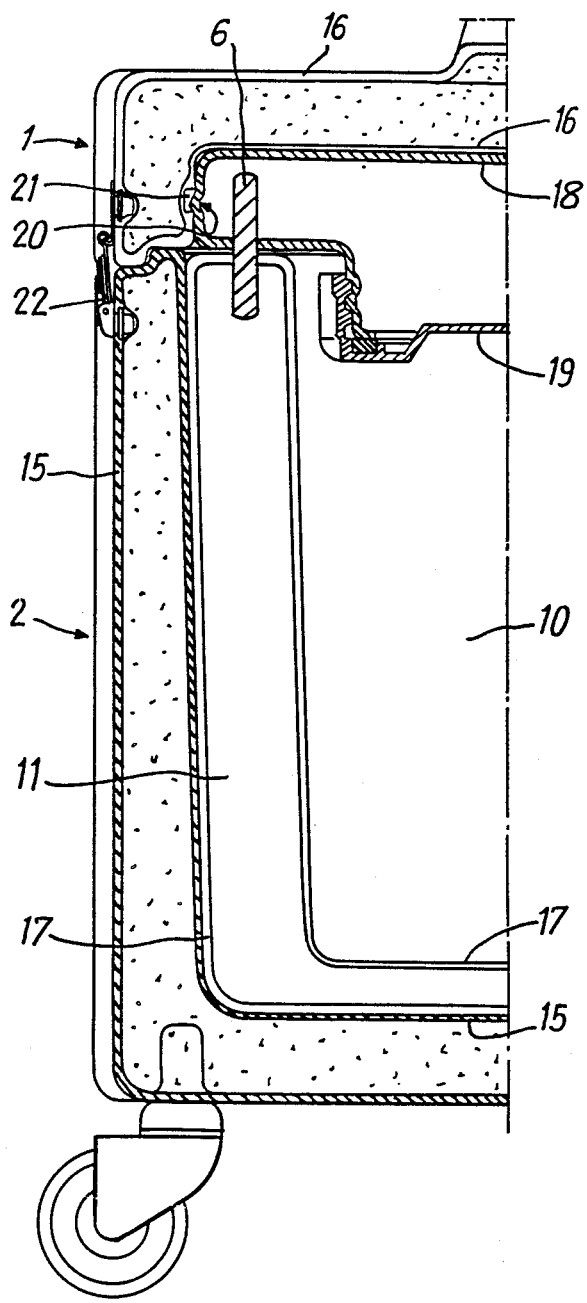

Reference is now made to FIG. 2 which represents an advantageous arrangement of the lid 1 and vessel 7.

The heat insulation of the vessel 7 is constituted by a hollow exterior case 15 made in a single piece, for example by a rotating moulding process (rotomoulding) and filled with an expanded polyurethane foam.

The heat insulation of the lid 1 is achieved in the same way. The reference 16 designates the exterior case of the latter which is filled with expanded polyurethane foam.

The peripheral enclosure 11, which defines a principal enclosure 10 receiving the graft, is constituted by a hollow case 17 made in a single piece by rotomoulding. When in position, the enclosure 11 is substantially in contact with the case 15. The enclosure 11 is removable. Handles (not shown), for example moulded in one piece, may be provided for facilitating the withdrawal and the placing in position.

The enclosure 2 for disposing the thermal source is also arranged to be removable. It is made in two parts, a moulded case 18 and a closing means 19. The moulded case 18 is provided with a lateral projection 20 which is adapted to come into engagement with a complementary recess 21 provided in the case 16 for maintaining the enclosure 2 in position in the lid.

The heat exchange device is identical to that of FIG. 1 Its assembly requires in addition a drilling operation on the wall of the peripheral enclosure 11. Apart from the passage of the metal members 6 for the heat exchange, the holes formed by the drilling are used to fill said enclosure 11 with refrigerated water.

The sealing of the peripheral enclosure 11 is simpler to ensure than in the preceding embodiment since it is sufficient to employ suitable 0-section sealing members (not shown).

If need be, the sealing of the assembly may be completed by the use of a peripheral sealing means.

Lastly, the closing of the container is advantageously achieved by an elastic device 22 of the spring type.

Figure 3:
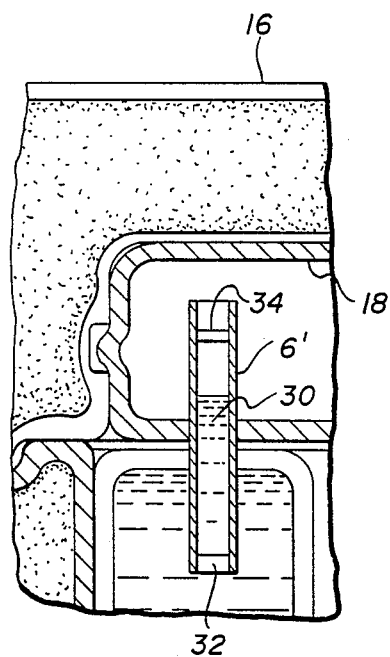

In the two described embodiments it will be understood that the metal members for the thermal exchange may be constituted either by simple metal studs as shown in FIGS. 1 and 2 or by hollow metal studs 6' shown in FIG. 3. Hollow studs 6' comprise a certain volume of a gas in the liquid state, such as butane 30. In the latter case, the studs 6 each include a filler 32 and a valve 34.

Furthermore, the container according to the invention is advantageously provided with exterior handles both on the vessel and on the lid, and stowing means, all of which are moulded in one piece, for example, so as to facilitate handling and transport.

It must be well understood that the invention is in no way limited to that described and that various modifications of form or material may be made therein without departing from the scope or spirit of the invention.

We claim:

1. A container for transporting grafts at 4° C. comprising:
    a vessel;
    a lid movable between a vessel-closing position and a vessel-opening position;
    insulating means for thermally insulating the vessel and lid from an exterior medium;
    means for defining a peripheral volume of water in the vessel including a layer located in an upper part of the volume of water;
    a thermal source at a constant temperature below 4° C. and superjacent the layer of water; and
    a thermal exchange located in an upper part of the container for providing a thermal exchange between the thermal source and the layer of water to maintain the volume of water at substantially 4° C.

2. Container according to claim 1, wherein said thermal exchanger is located in a lower part of the lid.

3. Container according to claim 1, wherein said peripheral volume of water is a water jacket.

4. Container according to claim 1, wherein said peripheral volume of water is a peripheral enclosure.

5. Container according to claim 1, wherein the lid comprises an enclosure for disposing the thermal source, means defining an opening in the enclosure for the thermal source for the introduction of the thermal source, and means for hermetically closing said opening.

6. Container according to claim 5, wherein the heat exchanger comprises members made from a metal which is a good thermal conductor, fixed relative to the lid and arranged in such a manner as to extend in a first direction into the enclosure containing the thermal source and to extend beyond the lid in a direction opposite to said first direction into an upper part of said peripheral volume of water when the lid is in said vessel-closing position.

7. Container according to claim 6, wherein said members are hollow metal studs containing a volume of gas in a liquid state, said gas being condensable in a gaseous state at substantially 0° C.

8. Container according to claim 7, wherein said gas is butane.

9. Container according to claim 6, wherein said metal members are made from an aluminum/magnesium alloy.

10. Container according to claim 6, wherein the container has an interior and a partition divides the interior into a principal enclosure for receiving the graft and a peripheral enclosure defining openings so arranged that the metal members of the thermal exchanger are capable of entering said openings when the lid is in said vessel-closing position.

11. Container according to claim 10, wherein insulating walls define respectively the lid and the vessel, and the enclosure for disposing the thermal source and the peripheral volume are removable relative to the insulating walls.

12. Container according to claim 10, wherein the peripheral volume has a relatively small thickness.

13. Container according to claim 10, wherein when a graft is placed inside the principal enclosure, the peripheral volume is filled with water at +4° C.

14. Container according to claim 10, wherein, when a graft is placed inside the principal enclosure, the peripheral volume is filled with water having a temperature which takes into account a thermal flow required for bringing the graft to a uniform temperature of about +4° C.

15. Container according to claim 5, wherein the enclosure containing the thermal source has a bottom which is not thermally insulated.

* * * * *